United States Patent [19]

Michel et al.

[11] Patent Number: 5,142,097

[45] Date of Patent: Aug. 25, 1992

[54] RECOVERY AND RECYCLE OF ACETIC ACID IN AN OXIDATION PROCESS

[75] Inventors: Robert E. Michel; Roger G. Rudolph, both of Wilmington, N.C.

[73] Assignee: E. I. Du Pont de Nemours and Company, Wilmington, Del.

[21] Appl. No.: 714,041

[22] Filed: May 31, 1991

[51] Int. Cl.⁵ .................... C07C 67/00; C07C 51/16; C07C 51/50
[52] U.S. Cl. ..................... 560/78; 562/409; 562/414; 562/608
[58] Field of Search .................. 562/409, 414, 608; 560/78

[56] References Cited

U.S. PATENT DOCUMENTS

| | | | |
|---|---|---|---|
| 2,459,014 | 1/1949 | Cavanaugh et al. | 560/98 |
| 4,158,738 | 1/1979 | Scott et al. | 562/416 |
| 4,268,690 | 5/1981 | Komatsu et al. | 562/416 |
| 4,729,818 | 3/1988 | Berg | 203/68 |
| 4,820,862 | 4/1989 | Hoffmann et al. | 560/77 |
| 5,008,450 | 4/1991 | Yamamoto et al. | 562/485 |

Primary Examiner—Jose G. Dees
Assistant Examiner—Vera C. Clarke
Attorney, Agent, or Firm—Earl L. Handley

[57] ABSTRACT

Acetic acid is recovered from the mother liquor used to oxidize para-xylene to terephthalic acid by adding at least one organic compound having a melting point below 140° C. and an atmospheric boiling point above 230° C.

4 Claims, No Drawings

RECOVERY AND RECYCLE OF ACETIC ACID IN AN OXIDATION PROCESS

FIELD OF THE INVENTION

This invention relates to a continuous process for the preparation of terephthalic acid (or alternatively to the preparation of dimethylterephthalate), by the air oxidation of p-xylene in an acetic acid based mother liquor, and more specifically to the recovery of the acetic acid from the mother liquor and to the recycle of the recovered acetic acid to the step of air oxidation of additional p-xylene where the recycled acetic acid again serves as a component of the mother liquor.

BACKGROUND OF THE INVENTION

There are many processes for the preparation of terephthalic acid by the oxidation of p-xylene. Many of the processes are carried out using an acetic acid mother liquor—see, for example, Scott et al. U.S. Pat. No. 4,158,738.

Dimethyl terephthalate is produced by the esterification of terephthalic acid, see U.S. Pat. No. 2,459,014.

Both terephthalic acid and dimethyl terephthalate are useful as monomers in the preparation of polyester fibers.

It is conventional to prepare terephthalic acid in a continuous process in which para-xylene is oxidized to terephthalic acid in an acetic acid based mother liquor. The terephthalic acid is separated from the mother liquor by crystallizing the terephthalic acid and the mother liquor recycled to the oxidizer where it serves as a mother liquor for additional para-xylene to be oxidized. The recycled stream contains other desirable components such as catalyst metals and some terephthalic acid (the amount that is soluble at the crystallization temperature) as well as undesirable components such as other oxidation products including phthalic acid, benzoic acid and isophthalic acid and unknown compounds that lend yellow color to the terephthalic acid. These undesirable components build up in the recycling stream to the extent that the oxidation and separation process becomes inefficient. To control this build up, the recycled stream is purged, for example, by distilling at least a portion of the stream to recover the acetic acid component and to remove the undesirable components. The recovered acetic acid is returned to the oxidizer, and the residue may be burned or otherwise disposed of. It is, of course, desirable to recover as much acetic acid from this purge stream as possible. Simple distillation of the purge stream allows recovery of some of the acetic acid, but a substantial portion remains in the residue.

An object of the present invention is to provide a process for the recovery of increased amounts of acetic acid from the purge stream.

SUMMARY OF THE INVENTION

The present invention is a continuous process for the preparation of terephthalic acid, or dimethyl terephthalate, which comprises the following steps in sequence:

oxidizing para-xylene in an acetic acid based mother liquor to form a mixture containing terephthalic acid, separating terephthalic acid from the resulting mixture, recovering acetic acid from the portion of the mixture remaining after removal of terephthalic acid by first adding to this mixture, at least one organic compound which is miscible with acetic acid, said organic compound having (a) a melting point below 140 degrees C., and
(b) an atmospheric pressure boiling point above 230 degrees C., then distilling acetic acid from the newly formed mixture, returning the distilled acetic acid to the step of oxidizing the para-xylene.

If desired the terephthalic acid may be esterified in the conventional manner to form dimethyl terephthalate. The at least one organic compound that is added to the portion of the mixture remaining after removal of the terephthalic acid include dimethyl terephthalate, dimethyl isophthalate, dimethyl phthalate, monobasic aliphatic carboxylic acids ranging from $C_8$ (octanoic acid) to $C_{22}$ (docosynoic acid), benzoic acid and/or methyl para-formyl benzoate. The added "at least one organic compound" may be a mixture of compounds, for example, a suitable additive is the mixture of compounds obtained when crude terephthalic acid obtained after crystallization from mother liquor, is esterified with methanol and then the dimethyl terephthalate separated from the resulting mixture. After separation of the dimethyl terephthalate, the remaining components include methyl para-formyl benzoate; i.e., the half ester of dimethyl terephthalate.

The amount of additive required to increase the acetic acid recovery efficiency depends on the kind and amount of other compounds present in the mixture, but in general the amount of additive plus the amount of benzoic acid should be on a weight basis at least two times the amount of terephthalic acid plus isophthalic acid in the mixture. Preferably, the ratio is between 2.5 and 6, and most preferably between 4 and 6.

The process of the invention may be used in a terephthalic acid process in which polymer grade product is produced, or in a terephthalic acid process in which the product is less pure and is esterified to form dimethyl terephthalate.

EXAMPLES

Four liters of mother liquor from a direct oxidation polymer grade terephthalic acid process which contained, along with other impurities, 0.5% benzoic acid, 0.2% terephthalic acid, 0.3% isophthalic acid, 14% water and about 83% acetic acid was continuously fed to a distillation system consisting of a 250 ml. three necked distillation pot equipped with a 6" Vigreux column topped with a distillation head, a thermometer, mechanical stirrer and heating mantle. Acetic acid-water was distilled until the pot temperature reached 140° C. In the first experiment nothing was added to the distillation and acetic acid-water removal was continued. When the pot temperature reached 160° C. the pot residue became very stiff and the stirrer stopped. Analysis showed that the system still contained 25% acetic acid.

In the next experiments, 30 g (a) of either a mixture of methyl para-formyl benzoate (MFB), and dimethyl terephthalate (DMT), (60% MFB, 40% DMT) or (b) benzoic acid was added to the distillation pot after the temperature reached 140° C. Thirty grams is about 40% of the calculated amount of non-volatile residue. The ratio of additive plus benzoic acid to terephthalic acid plus isophthalic acid was about 2.5. In both instances the residue remained fluid up to 210° C. Analysis showed that the system contained 5% acetic acid when the distillation was stopped at 210° C. In both instances the residue remained fluid up to 210° C.

An acetic acid based mother liquor stream from a process that makes a terephthalic acid to be esterified to dimethylterephthalate, contained 0.15% terephthalic acid, 0.35% isophthalic acid. The mother liquor also contained catalyst metals: 0.03% cobalt and 0.05% manganese, and also about 0.06% bromide. Enough of a mixture of methyl para-formyl benzoate (MFB) and dimethyl terephthalate (DMT) (about 60% MFB and 40% DMT) was added to bring the ratio of (a) benzoic acid plus additive to (b) terephthalic acid plus isophthalic acid to 4, and acetic acid was then distilled from the mixture. The residue contained about 5% acetic acid.

We claim:

1. A continuous process for the preparation of terephthalic acid which comprises the following steps in sequence:

oxidizing para-xylene in an acetic acid based mother liquor to form a mixture containing benzoic acid and terephthalic acid, separating terephthalic acid from the resulting mixture, recovering acetic acid from the portion of the mixture remaining after removal of terephthalic acid by first adding to this mixture, at least one organic compound selected from the group consisting of dimethylterephthalate, demethylphthalate, monobasic aliphatic carboxylic acids from $C_8$ to $C_{22}$, benzoic acid, and methyl para-formyl benzoate, in an amount such that the at least one organic compound plus the amount of benzoic acid is on a weight basis at least two times the amount of terephthalic acid plus isopthalic acid in the mixture, said organic compound being miscible with acetic acid, said at least one organic compound having (a) a melting point below 140 degrees C., and
   (b) an atmospheric pressure boiling point above 230 degrees C., then distilling acetic acid from the newly formed mixture, returning the distilled acetic acid to the step of oxidizing the para-xylene.

2. The process of claim 1 in which the added organic compound is selected from the class consisting of benzoic acid, and methyl para-formyl benzoate.

3. The process of claim 1 in which includes the additional steps of esterifying the terephthalic acid to dimethylterephthalate, and then separating the dimethylterephthalate.

4. The process of claim 1 in which the amount of at least one organic compound added plus the amount of benzoic acid in the mixture is on a weight basis between 4 and 6 times the amount of terephthalic acid plus isophthalic acid in the mixture.

* * * * *